US00PP21190P2

(12) United States Plant Patent
Smith

(10) Patent No.: US PP21,190 P2
(45) Date of Patent: Aug. 10, 2010

(54) ***ASTER* PLANT NAMED 'PINK YOMAGIC'**

(50) Latin Name: *Aster hybrida*
Varietal Denomination: Pink Yomagic

(75) Inventor: Mark A. Smith, Fort Myers, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/455,899

(22) Filed: Jun. 9, 2009

(51) Int. Cl.
*A01H 5/00* (2006.01)

(52) U.S. Cl. ..... Plt./355

(58) Field of Classification Search ..... Plt./355
See application file for complete search history.

*Primary Examiner*—Annette H Para
(74) *Attorney, Agent, or Firm*—S. Matthew Edwards

(57) ABSTRACT

A new *Aster* plant named 'Pink Yomagic' particularly distinguished by the upright, freely branching growth habit, dark green colored foliage, and purple-violet colored ray florets.

1 Drawing Sheet

Latin name of the genus and species of the plant claimed: *Aster hybrida.*

Varietal denomination: 'Pink Yomagic'.

BACKGROUND OF THE NEW PLANT

The present invention comprises a new *Aster*, botanically known as *Aster hybrida,* and hereinafter referred to by the variety name 'Pink Yomagic.'

The new cultivar 'Pink Yomagic' has an upright, freely branching growth habit, dark green colored foliage, and purple-violet colored ray florets.

'Pink Yomagic' originated as a natural whole plant mutation of the cultivar 'Yomagic,' U.S. Plant Pat. No. 15,690. 'Pink Yomagic' was discovered and selected by the inventor as a single flowering plant within a population of the parent cultivar in a controlled breeding program in Alva, Fla., in March 2007. The parent cultivar 'Yomagic' has purple flower color, is a few days faster to flower under natural season response, and is slightly smaller in plant size.

The first act of asexual reproduction of 'Pink Yomagic' was by vegetative cuttings in April 2007, in a controlled environment in Alva, Fla.

Horticultural examination of plants grown from cuttings of the new plant initiated in April 2007, and continuing thereafter, has demonstrated that the combination of characteristics as herein disclosed for 'Pink Yomagic' are firmly fixed and are retained through successive generations of asexual reproduction.

'Pink Yomagic' has not been observed under all possible environmental conditions. The phenotype may vary significantly with variations in environment such as temperature, light intensity and day length.

A Plant Breeder's Right for this cultivar was applied for in the Community Plant Variety Office on Jun. 19, 2008. 'Pink Yomagic' has not been made publicly available more than one year prior to the filing of this application.

BRIEF DESCRIPTION OF THE PHOTOGRAPHS

The accompanying photographic drawing shows typical flower and foliage characteristics of 'Pink Yomagic' with colors being as true as possible with an illustration of this type. The photographic drawing shows a flowering potted plant of the new variety with two plants in the pot, and a close-up of the flowers.

DETAILED BOTANICAL DESCRIPTION

The plant description and measurements were taken in Salinas, Calif. in May 2009 under natural light, and the aforementioned photographs were taken in Gilroy, Calif. in May 2009 in a greenhouse. These plants were started and grown in six inch pots, in Alva, Fla. and were shipped in May 2009 to California. Plants were grown under conditions which approximate those generally used in commercial potted *Aster* production, including the use of short day/long night treatments and the pinching of terminal apices. These plants used in the photograph and descriptions were about ten weeks old.

Color references are made to The Royal Horticultural Society Colour Chart (RHS) 2001.

BRIEF SUMMARY OF INVENTION

The following traits have been repeatedly observed and are determined to be basic characteristics of the new variety. The combination of these characteristics distinguishes this *Aster* as a new and distinct variety

TABLE 1

DIFFERENCES BETWEEN THE NEW VARIETY 'PINK YOMAGIC' AND A SIMILAR VARIETY

| | 'Pink Yomagic' | 'Patricia Ballard' (unpatented) |
|---|---|---|
| Flower size: | Smaller | Larger |
| Flower color: | Darker | Lighter |
| Natural season flowering response: | 3 days faster | 3 days slower |
| Plant habit: | Shorter, fuller and rounder | Taller, less full and round |
| Stem strength: | Stronger | Less strong |

Plant:

*Form, growth and habit.*—Upright and freely branching.

*Plant height* (*inflorescence included*).—25-28 cm.

*Plant width.*—26-29 cm.

*Garden performance and tolerance to weather.*—Very good.
*Crop time to flowering.*—About 10 weeks.

Roots:
*Number of days to initiate roots.*—10 days at about 22 degrees C.
*Number of days to produce a rooted cutting.*—16-18 at 22 degrees C.
*Type.*—Fine, fibrous, free branching.
*Color.*—RHS N155B but whiter.

Foliage:
*Arrangement.*—Alternate, simple, sessile.
*Immature, leaf color, upper surface.*—RHS 137A.
*Lower surface.*—RHS 137B.
*Mature, leaf color, upper surface.*—RHS 147A.
*Lower surface.*—Closest to RHS 147A, but a little lighter.
*Length.*—5.4-6.3 cm.
*Width.*—0.7-1.15 cm.
*Shape.*—Ligulate.
*Base shape.*—Clasping.
*Apex shape.*—Acute.
*Margin.*—Entire.
*Texture, upper surface.*—Glabrous.
*Lower surface.*—Glabrous.
*Color of venation, upper surface.*—RHS 147B.
*Lower surface.*—RHS 147B.

Stem:
*Quantity of lateral branches per plant.*—About 6-8, with an abundance of secondary branching.
*Color of stem.*—RHS 147A.
*Length of stem.*—20-23 cm.
*Diameter.*—0.2-0.3 cm.
*Length of internodes.*—1.0-1.2 cm.
*Texture.*—Glabrous.
*Color of peduncle.*—RHS 147A.
*Length of peduncle.*—2.5-5.0 cm.
*Peduncle diameter.*—0.1 cm.
*Orientation to branch.*—About 45 degrees.
*Texture.*—Glabrous.

Inflorescence:
*Type.*—Compositate type, solitary inflorescences borne terminally, disk and ray florets arranged acropetally on a capitulum.
*Blooming habit.*—Under natural conditions, plants flower In early September in the Northern Hemisphere.
*Quantity of inflorescences per plant.*—Approximately 70-80.
*Lastingness of individual blooms on the plant.*—Approximately 3 weeks after the colored bud stage.
*Fragrance.*—None.

Bud:
*Color.*—Closest to RHS 77A.
*Length.*—0.5-0.8 cm.
*Width.*—0.4-0.5 cm.
*Shape.*—Ovoid.
*Immature.*—Inflorescence.
*Diameter.*—2.4-2.5 cm.
*Color of ray florets.*—Closest to RHS N80A.
*Mature.*—Inflorescence.
*Diameter.*—2.0-3.3 cm.
*Depth.*—0.5 cm.
*Total disc diameter.*—0.7-0.9 cm.
*Receptacle height.*—0.4 cm.
*Receptacle diameter.*—0.5-0.6 cm.

Ray florets:
*Average quantity of florets.*—25-28.
*Color of florets, upper surface.*—Closest to RHS N80B and then fading to RHS N80C with some of the margins twisting and curling inward giving a lighter appearance.
*Lower surface.*—RHS N82D.
*Length.*—1.5-1.6 cm.
*Width.*—0.3 cm.
*Shape.*—Ligulate.
*Apex shape.*—Slightly emarginate.
*Margin.*—Entire.
*Texture, upper surface.*—Papillose.
*Lower surface.*—Papillose.

Disc florets:
*Average quantity of disc florets.*—Approximately 50.
*Color of florets.*—RHS 157D; and with very mature florets having a RHS 59C apex.
*Length.*—0.4-0.5.
*Width.*—0.1-0.15 cm.
*Shape.*—Tubular, elongated.
*Apex shape.*—Acute, 5 pointed.

Phyllaries:
*Quantity.*—20-24 arranged in 2-3 whorls.
*Color, upper surface.*—RHS 147A.
*Lower surface.*—RHS 147A.
*Length.*—0.4-0.6 cm.
*Width.*—0.15 cm.
*Shape.*—Lanceolate.
*Apex shape.*—Acute.
*Based.*—Truncate.
*Margins.*—Entire.
*Texture, upper surface.*—Mostly glabrous and glossy, with some hirsute mainly on the margins.
*Lower surface.*—Mostly glabrous and glossy, with some hirsute mainly on the margins.

Reproductive organs:
*Gynoecium.*—Present on both florets.
*Pistil length.*—0.7 cm.
*Style color.*—RHS 155A.
*Style length.*—About 0.5 cm.
*Stigma color.*—RHS 4C.
*Stigma shape.*—Bi-parted.
*Ovary color.*—RHS 155C.
*Androecium.*—Present only on disc florets.
*Color of filaments.*—Closest to RHS 1D.
*Length filaments.*—0.3 cm.
*Anther color.*—RHS 6D.
*Anther length.*—0.2 cm.
*Anther shape.*—Ligulate.
*Pollen amount.*—None observed.
*Fruit/seed set.*—Has not been observed.

Disease/pest resistance: Disease resistance, susceptibility and tolerance have not been fully observed on this new variety.

What is claimed is:

1. A new and distinct variety of *Aster* plant named 'Pink Yomagic,' substantially as illustrated and described herein.

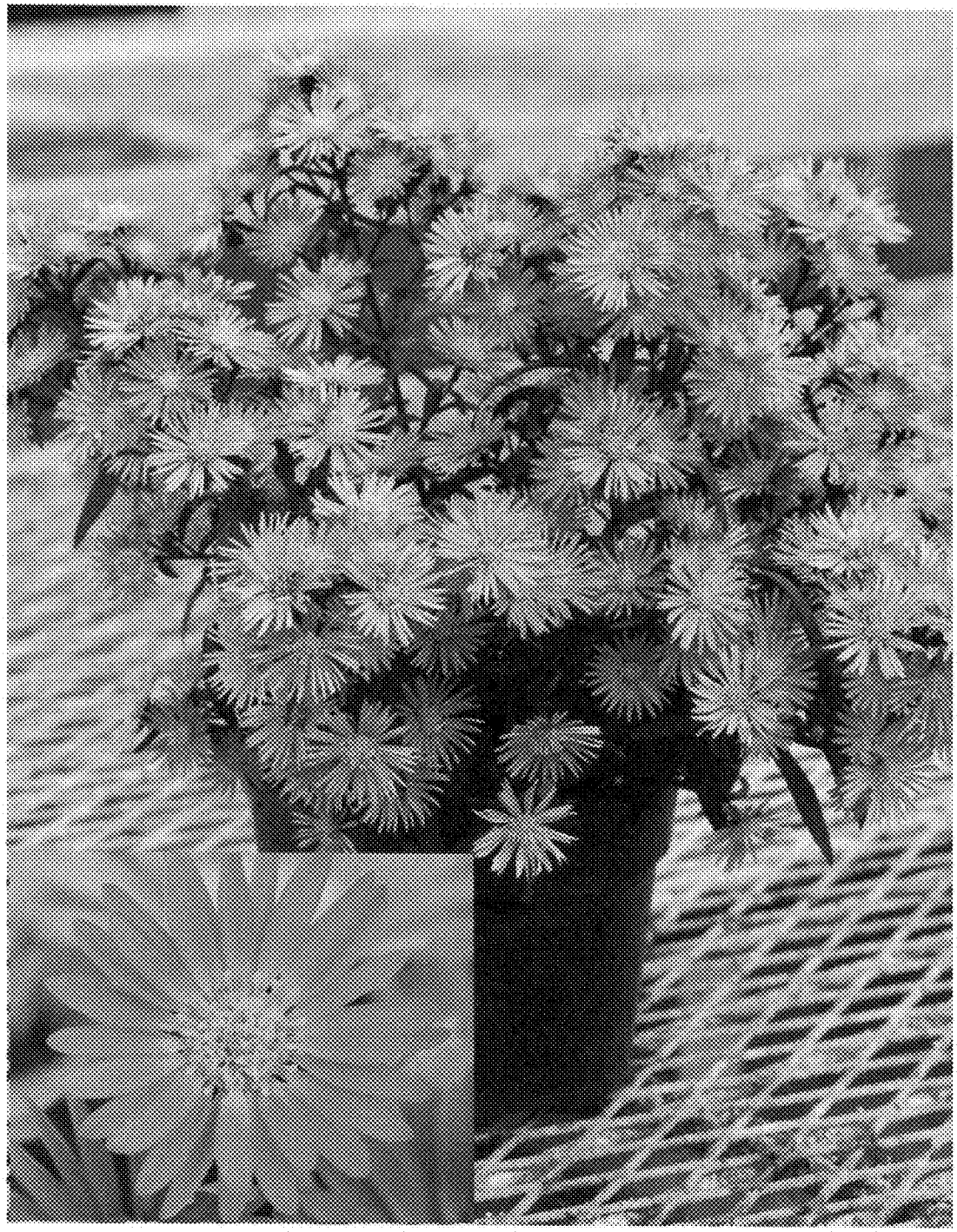

* * * * *